United States Patent [19]
Jasper

[11] Patent Number: 5,185,273
[45] Date of Patent: Feb. 9, 1993

[54] METHOD FOR MEASURING IONS IMPLANTED INTO A SEMICONDUCTOR SUBSTRATE

[75] Inventor: Craig L. Jasper, Phoenix, Ariz.

[73] Assignee: Motorola, Inc., Schaumburg, Ill.

[21] Appl. No.: 767,756

[22] Filed: Sep. 30, 1991

[51] Int. Cl.⁵ .............................. H01L 21/66
[52] U.S. Cl. .......................... 437/8; 437/7; 437/24; 148/DIG. 56
[58] Field of Search ........... 437/7, 8, 20, 24, 930; 148/DIG. 34, DIG. 40, DIG. 56, DIG. 162; 356/445; 374/5

[56] References Cited

U.S. PATENT DOCUMENTS

| | | | |
|---|---|---|---|
| 4,755,049 | 7/1988 | Bomback et al. | 356/30 |
| 4,799,392 | 1/1989 | Wilson et al. | 437/20 |
| 5,074,669 | 12/1991 | Opsal | 356/445 |

OTHER PUBLICATIONS

W. L. Smith et al., "Use of Thermal Waves to Measure Dose and Uniformity of Si+ and Be+ Implants into GaAs", SPIE, vol. 530, 1985.

Opsal et al., "Temporal Behavior of Modulated Optical Reflectance in Silicon", J. Appl. Phys., vol. 61, No. 1, Jan. 1987.

Primary Examiner—Brian E. Hearn
Assistant Examiner—C. Chaudhari
Attorney, Agent, or Firm—Joe E. Barbee

[57] ABSTRACT

A method is provided for correlating ion implantation from a silicon wafer (13) to a gallium arsenide wafer. A first dose of a predetermined amount of silicon ions is implanted into a silicon wafer (13). The first dose of the implanted silicon ions in the silicon wafer (13) is evaluated by a measuring system (10) that monitors a modulated reflected signal from the silicon wafer (13) and quantifies the signal as to the number of implanted silicon ions in the silicon wafer. If the measured quantity of implanted silicon ions is a desired amount of implanted silicon ions the same number of silicon ions is then implanted into the gallium arsenide wafer.

5 Claims, 1 Drawing Sheet

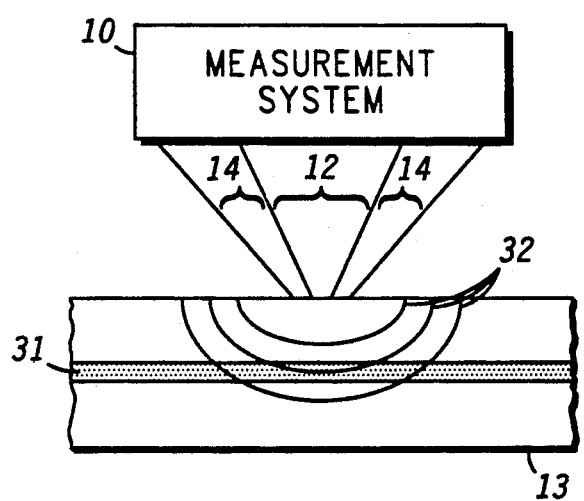

METHOD FOR MEASURING IONS IMPLANTED INTO A SEMICONDUCTOR SUBSTRATE

BACKGROUND OF THE INVENTION

This invention relates, in general, to semiconductor products, and more particularly, to manufacturing semiconductor devices.

At the present time, ions or dopants that are implanted into gallium arsenide substrates are not effectively and efficiently measured. These measurement inadequacies cause several problems, such as extended time delays for qualification of implanters, imprecise measurement of implanted dopants, and use of expensive gallium arsenide wafers.

Conventionally, measurement of ions implanted into gallium arsenide substrates is a multistep process. Typically, the gallium arsenide substrate is implanted with a specific dose or a specific number of ions. The substrate is then capped with a silicon nitride, a silicon dioxide, or a silicon oxynitride layer and subsequently annealed. The anneal activates the implanted ions and makes the implanted ions electrically measurable. The capping nitride layer is then stripped off the gallium arsenide substrate, thereby exposing the gallium arsenide substrate. A four-point probe is then used to measure the electrical activity in the gallium arsenide substrate that is a consequence of the implanted ions. This electrical activity, typically measured as ohms/square, is a result of the dose or the number of ions implanted into the gallium arsenide substrate. However, it should be realized that each ste is associated with a certain variability, and by having many steps the individual variability of each step is summed into a large total variation, thereby resulting in inaccurate measurement of implanted dopants.

For example, the anneal cycle, necessary for electrically activating the implanted ions, often does not produce complete activation of the implanted ions, thereby producing inaccurate electrical measurements which does not be directly correlated with the implanted ions. Inaccurate electrical measurements of the implanted ions are also caused by variations in substrate that the ions are implanted into. Additionally, high temperature furnace anneals may cause unwanted redistribution of dopants used to achieve desired electrical resistivity in the gallium arsenide substrate, thereby causing inaccurate electrical measurement of the ions implanted into the gallium arsenide wafer.

It can be readily seen that conventional measurement methods for determining dose of ion implantation into gallium arsenide substrates have severe limitations. Also, it is evident that the processing conditions required for measurement of ion implantation into gallium arsenide substrates adds to measurement variability. Additionally, because of the long processing time to prepare gallium arsenide substrates for measurement, it is not possible for immediate confirmation of an ion implanted dose from an ion implanting system. Therefore, a method for allowing a more accurate measurement of ion implantation for gallium arsenide substrates, as well as a shorter processing time for gallium arsenide substrates, would be highly desirable.

SUMMARY OF THE INVENTION

Briefly stated, a method is provided for correlating ion implantation from a silicon wafer to a gallium arsenide wafer. A dose of a predetermined amount of silicon ions is implanted into a silicon wafer. The dose of the implanted silicon ions in the silicon wafer is measured by a system that monitors a modulated reflected signal from the silicon wafer and quantifies the signal to the predetermined amount or number of implanted silicon ions in the silicon wafer. The measured quantity of implanted silicon ions is then used to directly correlate the number of silicon ions implanted into a gallium arsenide wafer.

BRIEF DESCRIPTION OF THE DRAWINGS

The single FIGURE is a simplified pictorial cross-sectional illustration of a thermal wave measurement system evaluating an implanted semiconductor substrate.

DETAILED DESCRIPTION OF THE DRAWINGS

The sole FIGURE is a simplified pictorial illustration of a thermal wave measurement system 10 measuring or evaluating a semiconductor substrate 13. Thermal wave measurement system 10 is a commercially available product made by Therma-Wave of Fremont, Calif. It should be understood that only a brief description of major components of measurement system 10 will be provided to orientate the reader. For a more detailed and theoretical description of measurement system 10, please refer to an article by Jon Aposal et al., "Temporal Behavior of Modulated Optical Reflectance in Silicon," *Journal of Applied Physics*, 61 (1) Jan. 1, 1987, pages 240–248, which is hereby incorporated by reference herein.

Generally, measurement system 10 uses two focused laser beams 12 and 14 to generate and to detect thermal waves or plasma waves 32 that are generated in semiconductor substrate 13. Measurement system 10 directs a modulated laser beam 12 to semiconductor substrate 13. Simultaneously, probe laser beam 14 is also directed to semiconductor substrate 13. Laser beam 12 and laser beam 14 are now focused at the same spot on semiconductor substrate 13 and thus are coincident on semiconductor substrate 13.

Probe laser beam 14 focused on semiconductor substrate 13 undergoes small modulations in its reflected power that result from thermal waves or plasma waves 32 that are induced into semiconductor substrate 13 from pump laser beam 12. Generally, pump laser beam 12 induces thermal waves or plasma waves 32 in semiconductor 13, which in return induce variations or modulations in local dielectric constant of semiconductor substrate 13. Variation or modulation of the dielectric constant results in changes in the reflectivity of semiconductor substrate 13. The modulation or variation is measured by monitoring a reflected intensity of probe laser beam 14 with a detector in therma-wave measurement system 10.

It should be understood that only a small portion of semiconductor substrate 13 is shown and that other portions of semiconductor substrate 13 can be measured. In the present invention, a method is provided for measuring implanted ions in semiconductor substrate 13 in which the implanted ions are of a similar dopant type, as is semiconductor substrate 13 into which the ions are implanted.

In one embodiment of the present invention, semiconductor substrate 13 is made of either n-type or p-type material, and implanted ions or dopants of similar types are implanted into similar typed substrates. For example, an n-type substrate 13 is implanted with an n-type dopant. It should be understood that measurement of implanted ions is achieved directly after implantation into substrate 13 and that it is not necessary to anneal substrate 13 or treat substrate 13 in any other manner. Measurement of the number of implanted ions is accomplished by placing implanted substrate 13 into measurement system 10 and measuring the number of ions in substrate 13 by using measurement system 10 which measures thermal waves. Since thermal waves respond proportionally to an amount of damage that is caused by the amount of ions implanted, measurement system 10 responds to implant damage caused by the implanted ions with a characteristic response that is reflected and recorded by measurement system 10, thereby allowing for measurement of ions that are implanted into electrically similar substrates.

By way of example, with semiconductor substrate 13 made of silicon and implanted ions 32 made of either silicon, magnesium, or beryllium, measurement of implanted silicon ions, magnesium ions, or beryllium ions in silicon wafer 13 is accomplished by placing silicon wafer 13 into a thermal wave measurement system 10. Thermal wave measurement system 10 uses two focused laser beams 12 and 14, which are directed onto a top surface of silicon substrate 13. Laser beam 14 induces thermal waves 32, which propagate through silicon wafer 13. When thermal waves 32 contact damaged layer 31, a change in refractive indexes occurs at the surface of silicon wafer 13, which is detected by probe laser beam 14. These changes in refractive index are reflected back to the detector and are subsequently quantified. Thus, using the present invention, a method is provided for measuring silicon, magnesium, or beryllium ions that are implanted in a silicon wafer that does not produce an electrically active junction. Additionally, a method for measuring implanted dopant levels or the number of implanted ions is achieved without sensing an electrical junction in substrate 13, which is usually done by conventional four-point probes or spreading resistance probes. Also, the conventional multistep process, which is required to form an electrically active junction, such as a pn junction, a np junction, or schottky diode is not necessary using the present invention. Further, by using the present invention, a long preparation time which is necessary for the multistep process is greatly reduced to a single step.

In order to make semiconductor devices, ions are implanted into semiconductor substrates to provide a source of impurities to make electrically active junctions for semiconductor devices. It should be understood that the semiconductor devices are built in accordance with common practice in the semiconductor art that is not discussed herein. These implanted ions require precise measurement to insure that a correct number of ions or dose of ions is given to the semiconductor substrate in order to obtain a correctly performing semiconductor device. However, accurate measurement of the dose or the number of ions is a severe problem when implanting the ions into gallium arsenide. Additionally, speed at which measurements of the dose or the number of ions that can be measured is also a problem for gallium arsenide substrates, as has been previously discussed.

In another embodiment of the present invention, silicon wafer 13 is used as an implant correlation device for implantation of gallium arsenide wafers (not shown). Silicon wafer 13 is implanted with either silicon, magnesium, or beryllium ions in a predetermined dose from an ion implanter (not shown) prior to implantation of gallium arsenide wafers with the same predetermined dose. Implanted silicn wafer 13 is measured by thermal wave measurement system 10. Once measurement is completed and the correct dose has been verified the gallium arsenide wafers are subsequently implanted. Additionally, if an incorrect dose is measured, suitable corrective action may be taken before implantation of the gallium arsenide wafers, thereby reducing an opportunity for an incorrect implant of ions into the gallium arsenide wafers. Further, it should be realized that the sequence of implanting a silicon wafer and measuring the implanted silicon wafer can be done a multitude of times to verify the correct dose. By using this embodiment of the present invention, a real time or an immediate verification of implant dose is achieved. Additionally, measurement of silicon correlation wafer 13 is accomplished with greater precision and greater accuracy than by measuring either a gallium arsenide test wafer using measurement system 10 or by measuring a gallium arsenide test wafer using the multi-step process previously described. Greater accuracy of measuring implanted ions in the silicon test wafer is achieved for several reasons, such as less variation in the silicon substrate, which facilitates measurement, and fewer processing steps which curtail process variations. Further, the measurement is sensitive to minority carrier lifetime. Minority carrier lifetime is higher for undamaged silicon than for gallium arsenide. Consequently, processes such as ion implantation, that degrade minority carrier lifetime have a greater relative effect on silicon than on gallium arsenide. Also, a large cost savings is realized because silicon wafer 13 is much cheaper than a gallium arsenide wafer. Further, there is a substantial reduction in measurement time, as well as an assurance that a correct dose will be implanted into subsequent gallium arsenide wafers.

By now it should be appreciated that a novel method for correlating ion implantation from a silicon wafer to a gallium arsenide wafer has been described. The method allows for greater precision and greater accuracy in measuring the implanted dopants. Additionally, the method allows for a large cost savings to be realized because silicon wafers are less expensive than gallium arsenide wafers.

I claim:

1. A method for correlating ion implantation from a silicon wafer to a gallium arsenide wafer comprising:
   implanting a dose of a predetermined amount of ions into a silicon wafer;
   measuring the dose of implanted ions in the silicon wafer by a measuring system that monitors a modulated reflected signal from the silicon wafer that quantifies the signal to a number of ions implanted into the silicon wafer;
   using the measured quantity of the implanted ions in the silicon wafer to determine when a desired amount of ions have been implanted into the silicon wafer; and
   implanting a dose of the same predetermined amount of ions into a gallium arsenide wafer.

2. The method of claim 1 wherein the implanting of the ions is achieved by implanting silicon ions into the silicon substrate.

3. The method of claim 1 wherein the implanting of the ions is achieved by implanting magnesium ions into the silicon substrate.

4. A method for accurately verifying set-up of an ion implanter for subsequent ion implantation of gallium arsenide wafers:

implanting a silicon test wafer with a silicon dose from the ion implanter;

measuring the silicon dose in the test wafer in a thermal-Wave measurement system;

verifying the dose in the silicon test wafer is correct; and implanting the gallium arsenide wafer with the same dose.

5. The method of claim 1 wherein the implanting of the ions is achieved by implanting beryllium ions into the silicon substrate.

* * * * *